US011883089B2

(12) United States Patent
Cheng et al.

(10) Patent No.: US 11,883,089 B2
(45) Date of Patent: *Jan. 30, 2024

(54) CONTROLLED OPTICAL PROPERTIES VITREOUS ENAMEL COMPOSITION FOR ELECTROSURGICAL TOOL

(71) Applicant: Medtronic Advanced Energy LLC, Minneapolis, MN (US)

(72) Inventors: Xiaoming Cheng, Keller, TX (US); William X. Siopes, Jr., Tyngsborough, MA (US)

(73) Assignee: Medtronic, Inc., Minneapolis, MN (US)

( * ) Notice: Subject to any disclaimer, the term of this patent is extended or adjusted under 35 U.S.C. 154(b) by 93 days.

This patent is subject to a terminal disclaimer.

(21) Appl. No.: 16/327,215

(22) PCT Filed: Nov. 14, 2017

(86) PCT No.: PCT/US2017/061626
§ 371 (c)(1),
(2) Date: Feb. 21, 2019

(87) PCT Pub. No.: WO2018/090046
PCT Pub. Date: May 17, 2018

(65) Prior Publication Data
US 2019/0185370 A1    Jun. 20, 2019

Related U.S. Application Data

(60) Provisional application No. 62/421,895, filed on Nov. 14, 2016.

(51) Int. Cl.
*A61B 18/14*    (2006.01)
*C03C 3/066*    (2006.01)
(Continued)

(52) U.S. Cl.
CPC .......... *A61B 18/14* (2013.01); *A61B 18/1206* (2013.01); *A61B 18/1402* (2013.01);
(Continued)

(58) Field of Classification Search
None
See application file for complete search history.

(56) References Cited

U.S. PATENT DOCUMENTS 3,285,773 A    11/1966   Dunning et al.
3,510,343 A     5/1970   Twells et al.
(Continued)

FOREIGN PATENT DOCUMENTS

CN    101054312    10/2007
DE    102016111390    12/2017
(Continued)

OTHER PUBLICATIONS

"ASM standard gloss levels", 2020 (Year: 2020).*
(Continued)

*Primary Examiner* — Humera N. Sheikh
*Assistant Examiner* — Elizabeth D Ivey
(74) *Attorney, Agent, or Firm* — Patterson Thuente, P.A.

(57) ABSTRACT

A vitreous enamel coating for an electrosurgical metal cutting blade, in which incident light striking the vitreous enamel coating is diffusely reflected or absorbed, and the vitreous enamel coating exhibits a 60° gloss value less than 100 gloss units as measured according to ASTM D523-14, Standard Test Method for Specular Gloss. The coating reduces glare from light sources such as a nearby plasma-mediated discharge, operating theater lights or lights provided on an electrosurgery apparatus. The coating may also lessen interference with markers, sensors or other instruments designed to measure light emitted by or passing through nearby tissue such as by transillumination.

19 Claims, 10 Drawing Sheets

(51) Int. Cl.

| | |
|---|---|
| *C03C 3/091* | (2006.01) |
| *C03C 8/02* | (2006.01) |
| *C03C 3/093* | (2006.01) |
| *C03C 8/04* | (2006.01) |
| *C03C 3/064* | (2006.01) |
| *A61L 31/14* | (2006.01) |
| *C03C 4/02* | (2006.01) |
| *C03C 8/14* | (2006.01) |
| *C03C 10/00* | (2006.01) |
| *C03C 8/16* | (2006.01) |
| *A61L 31/02* | (2006.01) |
| *C03C 4/16* | (2006.01) |
| *A61B 18/12* | (2006.01) |
| *A61B 18/00* | (2006.01) |

(52) U.S. Cl.
CPC .......... *A61B 18/148* (2013.01); *A61L 31/026* (2013.01); *A61L 31/14* (2013.01); *C03C 3/064* (2013.01); *C03C 3/066* (2013.01); *C03C 3/091* (2013.01); *C03C 3/093* (2013.01); *C03C 4/02* (2013.01); *C03C 4/16* (2013.01); *C03C 8/02* (2013.01); *C03C 8/04* (2013.01); *C03C 8/14* (2013.01); *C03C 8/16* (2013.01); *C03C 10/00* (2013.01); *C03C 10/0036* (2013.01); *C03C 10/0054* (2013.01); *A61B 2018/00083* (2013.01); *A61B 2018/00107* (2013.01); *A61B 2018/00125* (2013.01); *A61B 2018/00148* (2013.01); *A61B 2018/00601* (2013.01); *A61B 2018/00607* (2013.01); *A61B 2018/126* (2013.01); *A61B 2018/1253* (2013.01); *A61B 2018/1412* (2013.01); *A61B 2018/1415* (2013.01); *C03C 2204/00* (2013.01)

(56) References Cited

U.S. PATENT DOCUMENTS

| | | | |
|---|---|---|---|
| 4,582,056 A | 4/1986 | McCorkle et al. | |
| 4,732,794 A | 3/1988 | Hyde | |
| 4,820,545 A * | 4/1989 | Negrych | C04B 41/009 |
| | | | 216/101 |
| 5,393,714 A | 2/1995 | Thometzek et al. | |
| 5,423,806 A | 6/1995 | Dale et al. | |
| 5,573,529 A | 11/1996 | Haak et al. | |
| 5,776,613 A | 7/1998 | Shimatani et al. | |
| 5,779,715 A | 7/1998 | Tu | |
| 5,980,515 A | 11/1999 | Tu | |
| 6,033,402 A | 3/2000 | Tu et al. | |
| 6,071,283 A | 6/2000 | Nardella et al. | |
| 6,080,152 A | 6/2000 | Nardella et al. | |
| 6,135,998 A | 10/2000 | Palanker | |
| 6,183,469 B1 | 2/2001 | Thapliyal et al. | |
| 6,241,692 B1 | 6/2001 | Tu et al. | |
| 6,379,351 B1 | 4/2002 | Thapliyal et al. | |
| 6,419,674 B1 | 7/2002 | Bowser et al. | |
| 6,569,510 B1 * | 5/2003 | Menon | B32B 15/04 |
| | | | 359/883 |
| 6,616,744 B1 | 9/2003 | Sainz et al. | |
| 6,623,437 B2 | 9/2003 | Hinchliffe et al. | |
| 6,712,817 B1 | 3/2004 | Goto et al. | |
| 7,107,105 B2 | 9/2006 | Bjorklund et al. | |
| 8,128,636 B2 | 3/2012 | Lui et al. | |
| 8,192,430 B2 | 6/2012 | Goode et al. | |
| 8,428,747 B2 | 4/2013 | Coe et al. | |
| 8,439,910 B2 | 5/2013 | Greep et al. | |
| 8,480,696 B2 | 7/2013 | Clague et al. | |
| 8,632,558 B2 | 1/2014 | Chin et al. | |
| 9,023,040 B2 | 5/2015 | Bloom et al. | |
| 9,028,520 B2 | 5/2015 | Taylor et al. | |
| 9,149,290 B2 | 10/2015 | Goode et al. | |
| 9,155,878 B2 | 10/2015 | Goode et al. | |

| | | | |
|---|---|---|---|
| 2003/0129329 A1 * | 7/2003 | Grossman | C23C 30/00 |
| | | | 428/34.1 |
| 2004/0087939 A1 | 5/2004 | Eggers et al. | |
| 2004/0129329 A1 | 7/2004 | Kondou et al. | |
| 2004/0151745 A1 | 8/2004 | Zimmer et al. | |
| 2005/0149096 A1 | 7/2005 | Hilal et al. | |
| 2007/0005057 A1 | 1/2007 | Heim et al. | |
| 2008/0027428 A1 * | 1/2008 | Palanker | A61B 18/1402 |
| | | | 606/45 |
| 2010/0009203 A1 | 1/2010 | Nageno et al. | |
| 2010/0129726 A1 | 5/2010 | Tanida et al. | |
| 2010/0198229 A1 | 8/2010 | Olomutzki et al. | |
| 2010/0222787 A1 | 9/2010 | Goode et al. | |
| 2012/0171420 A1 | 7/2012 | Molins et al. | |
| 2012/0191084 A1 | 7/2012 | Davison et al. | |
| 2012/0282407 A1 * | 11/2012 | Singh | C03C 3/118 |
| | | | 427/376.3 |
| 2013/0065250 A1 * | 3/2013 | Hubbard | A61K 6/25 |
| | | | 435/7.8 |
| 2013/0183489 A1 | 7/2013 | Cremer et al. | |
| 2013/0226176 A1 | 8/2013 | Kuehner et al. | |
| 2014/0031800 A1 | 1/2014 | Ben et al. | |
| 2014/0276696 A1 | 9/2014 | Schneider | |
| 2014/0276770 A1 | 9/2014 | Ellman | |
| 2014/0276926 A1 | 9/2014 | Hendrick | |
| 2014/0296897 A1 | 10/2014 | Sotak et al. | |
| 2015/0031524 A1 | 1/2015 | Takayama | |
| 2016/0022302 A1 | 1/2016 | Olomutzki et al. | |
| 2016/0225966 A1 | 8/2016 | Maloney et al. | |
| 2018/0028258 A1 | 2/2018 | Zamarripa et al. | |
| 2019/0112225 A1 | 4/2019 | Mix et al. | |
| 2019/0185370 A1 | 6/2019 | Cheng et al. | |
| 2019/0192213 A1 | 6/2019 | Cheng et al. | |

FOREIGN PATENT DOCUMENTS

| | | | | |
|---|---|---|---|---|
| EP | 1903957 B1 | 12/2011 | | |
| ES | 2350943 T3 * | 1/2011 | ........... | C04B 41/009 |
| GB | 1465372 A | 2/1977 | | |
| WO | WO-2009046002 A1 | 4/2009 | | |

OTHER PUBLICATIONS

Gloss Testing Equipment Angle Selection; https://www.linshangtech.com/tech/tech489.html; Oct. 15, 2019 (Year: 2019).*
Gloss and Sheen (and drywall finishing levels required ); Master Painters Institute; http://www.paintinfo.com/mpi/approved/sheen.shtml; Apr. 2, 2021 (Year: 2021).*
Britannica Online Enciclopedia ; https://www.britannica.com/ ; corundum, hematite, olivine, pyrochlore, rutile, spinel, garnet Nov. 3, 2021 (Year: 2021).*
Translation—ES-2350943-T3; Gendronneau D; Jan. 2011 (Year: 2011).*
Extended European Search Report for European Application No. EP17869561.5, dated Apr. 3, 2020, 6 pages.
International Preliminary Report on Patentability for Application No. PCT/US2017/061615, dated May 23, 2019, 8 pages.
International Preliminary Report on Patentability for Application No. PCT/US2017/061623, dated May 23, 2019, 9 pages.
International Preliminary Report on Patentability for Application No. PCT/US2017/061626, dated May 23, 2019, 7 pages.
International Search Report and Written Opinion for Application No. PCT/US2017/061615, dated Feb. 6, 2018, 11 pages.
International Search Report and Written Opinion for Application No. PCT/US2017/061623, dated Jan. 29, 2018, 10 pages.
International Search Report and Written Opinion for Application No. PCT/US2017/061626, dated Mar. 8, 2018, 9 pages.
Neuzil P., et al., "Pacemaker and ICD Lead Extraction with Electrosurgical Dissection Sheaths and Standard Transvenous Extraction Systems: Results of a Randomized Trial," EP Europace, vol. 9, Issue—2, Feb. 2007, pp. 98-104.
Okamoto Y., et al., "Extraction of Recalled Riata Leads," The Journal of Innovations in Cardiac Rhythm Management, Jul. 4, 2013, pp. 1305-1314.

(56) References Cited

OTHER PUBLICATIONS

Perfecta, "Electrosurgical Dissection System," Cook Vascular Incorporated, Jan. 2013, pp. 1-144.
U.S. Appl. No. 16/334,233, filed Mar. 18, 2019, Inventor(s): Cheng et al.
U.S. Appl. No. 16/327,210, filed Feb. 21, 2019, Inventor(s): Cheng et al.
U.S. Appl. No. 15/662,450, filed Jul. 28, 2017, Inventor(s): Zamarripa et al.
Office Action from related EP Application No. 17808685.6, dated Oct. 4, 2022, 4 pgs.
Ceramic Technology, Jiaju Li et al., p. 225, China Light Industry Press, Jun. 2006, edition 1. No English translation available. Concise statement of relevance included in concurrently filed Supplemental Information Disclosure Statement transmittal.
Civil Engineering Materials, Xinquan Ni et al., p. 281, Wuhan University Press, Jan. 2014, edition 1, No English translation available. Concise statement of relevance included in concurrently filed Supplemental Information Disclosure Statement transmittal.
Civil Engineering Materials, Yamei Zhang et al., p. 279, Southeast University Press, Jan. 2013, edition 4, No English translation available. Concise statement of relevance included in concurrently filed Supplemental Information Disclosure Statement transmittal.
"Borosilicate Glass," Skyline Components, LLC., Aug. 15, 2022, 1 page [Borosilicate Glass, Aug. 15, 2011 (Year: 2011)].
Borosilicate Glass, Skyline Components, Retrieved from the Internet: <www.skylinecomponents.com/Borosilicate.html> on Jan. 11, 2023, 2 pages [Borosilicate Glass Proof of Date (Year: 2023)].
Borosilicate Material Properties, Retrieved from the Internet: <https://adamschittenden.com/technical/material-prop>, Nov. 18, 2009, 1 page [Borosilicate Material Properties, Nov. 18, 2009 (Year: 2009)].
Borosilicate Material Properties, Adams & Chittenden Scientific Glass Coop, 2003, 7 pages [Borosilicate Material Properties Proof of Date (Year: 2023)].
Temperature Expansion Coefficients, Retrieved from the Internet: <https://engineeringtoolbox.com/thermal-expansion>, May 10, 2010, 1 page [Linear Expansion Coefficients (Year: 2010)].
Thermal Expansion—Linear Expansion Coefficients, The Engineering ToolBox, 7 pages, 2023 [Linear Expansion Coefficients Proof of Date (Year: 2023)].

\* cited by examiner

800 °C/15 min.    850 °C/15 min.

800 °C/15 min.

830 °C/15 min.

850 °C/15 min.

870 °C/15 min.

CONTROLLED OPTICAL PROPERTIES VITREOUS ENAMEL COMPOSITION FOR ELECTROSURGICAL TOOL

CROSS-REFERENCE TO RELATED APPLICATIONS

This application is a National Phase entry of International Application Serial Number PCT/US2017/061626 filed Nov. 14, 2017 and entitled "CONTROLLED OPTICAL PROPERTIES VITREOUS ENAMEL COMPOSITION FOR ELECTROSURGICAL TOOL", which claims the benefit of U.S. Provisional Application Ser. No. 62/421,895 filed Nov. 14, 2016 and entitled "ENAMEL COMPOSITION FOR ELECTROSURGICAL TOOL", the disclosures of which are incorporated herein by reference in their entireties.

FIELD OF THE INVENTION

This invention relates to vitreous enamel compositions for coating electrosurgical cutting blades, and to the coated blades and methods for their manufacture and use.

BACKGROUND

Certain electrosurgical cutting equipment utilizes plasma energy to dissect tissue and coagulate blood vessels while producing minimal collateral damage to surrounding tissue. The cutting blade designed for the electrosurgical application often employs an insulating layer on a portion of the cutting blade to prevent energy from dispersing onto the bulk surface of the blade. Additionally, the insulating layer typically defines an uninsulated cutting edge (viz., an exposed electrode). The cutting edge, upon the introduction of a certain pattern of radiofrequency (RF) waveform, creates a substantially uniform and focused electrical field that upon contact with the cells in tissue forms a plasma-mediated discharge.

Despite improvements, there remains a need for even better vitreous enamel coatings for electrosurgical cutting blades. Such vitreous enamel coatings are disclosed and claimed herein.

SUMMARY

Vitreous enamel coatings may be formed from a glass frit that is melted atop a metal substrate and optionally heat processed to alter the physical properties, crystallinity or other characteristics of the resulting vitreous enamel. In some embodiments, the coating is delivered onto the metal substrate through a slurry which is formed by combining glass frit powders, binder, and solvent. The binder and solvent can be initially burned off in a burn-out process and the coating subsequently fired at elevated temperatures to form the vitreous enamel insulating layer on the metal substrate. For both the glass frit and slurry processes, the final vitreous enamel coating is derived from a melt, and upon cooling will have a characteristically smooth, glassy surface that provides strong specular reflection of incident light. Specular reflections may arise from the nearby plasma, from illumination sources on the electrosurgical device, or from the strong overhead illumination sources usually present in an operating theater or worn by a surgeon. These specular reflections can represent an objectionable source of glare, and may compromise surgical effectiveness during delicate or difficult to see surgical procedures.

Electrosurgical blades available from Medtronic traditionally employ a translucent black vitreous enamel coating, with a typical coating thickness of about 100 µm. Typically, the degree of translucency is such that the underlying metal substrate, including grinding or polishing marks, can be seen through the coating. During use, incident light passing through the vitreous enamel coating may strike the polished metal substrate and be specularly reflected back through the coating. Depending on a nearby individual's angle of view, a specular second surface reflection from the underlying substrate may represent an additional objectionable source of glare.

Light penetrating a translucent vitreous enamel coating may also heat up the underlying metal substrate. Although some heating is inevitably part of the plasma discharge process, and although temperatures may reach as high as 800° C. at the cutting edge, it nonetheless is desirable to avoid excessive heating in order to prolong blade life and reduce deterioration of the vitreous enamel or other insulative coating.

Some electrosurgical blades include an organic coating layer (e.g., of polytetrafluoroethylene (PTFE), polyurethane or silicone resin) disposed over the blade substrate. For example, electrosurgical blades available from Megadyne traditionally employ a green-tinted opaque PTFE coating, with the same shade of green being employed on all blades. The green coating has been made the subject of Trademark Registration No. 2021699. An organic coating may burn off during use, and may produce odors, smoke or volatile products of degradation or combustion that may be objectionable to a surgeon, other operator or other personnel in the operating theater.

The glare and heat problems mentioned above may be ameliorated or overcome by taking measures to manage or control incident light. The present invention accordingly provides in one aspect an article comprising:

(a) an electrosurgical cutting blade comprising a metal electrode, and (b) a visible vitreous enamel coating on at least a portion of the metal electrode, wherein incident light striking the vitreous enamel coating is diffusely reflected or absorbed, and the vitreous enamel coating exhibits a 60° gloss value less than 100 gloss units as measured according to ASTM D523-14, Standard Test Method for Specular Gloss.

The invention provides in another aspect a visible diffusely reflective or absorptive vitreous enamel coating formed from glass frit, wherein the coating is disposed on a metal electrode for an electrosurgical cutting blade and exhibits a 60° gloss value less than 100 gloss units as measured according to ASTM D523-14, Standard Test Method for Specular Gloss.

The invention provides in yet another aspect a method comprising providing a vitreous enamel precursor, applying the vitreous enamel precursor onto at least a portion of a metal electrode suitable for use as an electrosurgical cutting blade, and firing the vitreous enamel precursor to form a visible diffusely reflective or absorptive vitreous enamel coating that exhibits a 60° gloss value less than 100 gloss units as measured according to ASTM D523-14, Standard Test Method for Specular Gloss.

The disclosed electrosurgical cutting blade may be connected to a power source on an electrosurgical generator. The invention thus provides in another aspect a method comprising intermittently supplying radiofrequency energy to an electrosurgical cutting blade having a visible diffusely reflective or absorptive vitreous enamel coating that exhibits a 60° gloss value less than 100 gloss units as measured according to ASTM D523-14, Standard Test Method for Specular Gloss, to create a plasma-mediated discharge.

In preferred embodiments of the above-described article, coating and methods, the vitreous enamel coating exhibits a 60° gloss value less than 80, less than 60, less than 40, less than 20 or less than 10 gloss units. In certain additional embodiments, the vitreous enamel coating is sufficiently diffusely reflective or absorptive so that the underlying metal electrode is not visible through the coating under typical indoor illumination. In other additional embodiments, the vitreous enamel coating is sufficiently diffusely reflective or absorptive so that a specular second surface reflection from the underlying metal electrode is not visible through the coating during plasma operation.

In some embodiments of the above-described article, coating and methods, the vitreous enamel coating diffusely reflects or absorbs light in a visible light wavelength band of interest. In further embodiments, the vitreous enamel coating diffusely reflects or absorbs light in an infrared light wavelength band of interest, or in both visible and infrared wavelength bands of interest.

In some embodiments of the above-described article, coating and methods, a visible outer surface of the vitreous enamel coating is etched or otherwise roughened so that it will not specularly reflect incident light. In some embodiments, the vitreous enamel coating contains sufficient crystallinity, sufficient refractive inorganic pigment or sufficient colorants added to the glass frit so that the coating will absorb or scatter incident light. In some embodiments, the surface of the metal electrode is etched or otherwise roughened so that incident light passing into the vitreous enamel coating will not be specularly reflected by the metal electrode. In some embodiments a suitable non-specularly reflective coating (for example, a sol-gel coating) is applied between the metal electrode and the vitreous enamel coating, so that incident light passing into the vitreous enamel coating will not be specularly reflected by the metal electrode.

In some embodiments of the above-described article, coating and methods, the surface of the vitreous enamel coating is air-exposed and consequently is visible to an ordinary observer. In other embodiments, the vitreous enamel coating is covered with one or more transparent or translucent organic or preferably inorganic layers through which the vitreous enamel coating is visible to an ordinary observer. Preferably the outermost surface of such an organic or inorganic layer is etched or otherwise roughened so that it will not specularly reflect incident light.

The above summary of the present invention is not intended to describe each disclosed embodiment or every implementation of the present invention. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

The details of one or more embodiments of the invention are set forth in the description below. Other features, objects, and advantages of the invention will be apparent from the description, drawing, and from the claims.

BRIEF DESCRIPTION OF THE DRAWING

In the accompanying Drawing.

Like reference symbols in the various figures of the Drawing indicate like elements. The elements in FIG. 1 and FIG. 3 through FIG. 5 are not to scale.

SELECTED DEFINITIONS

Figure 1:
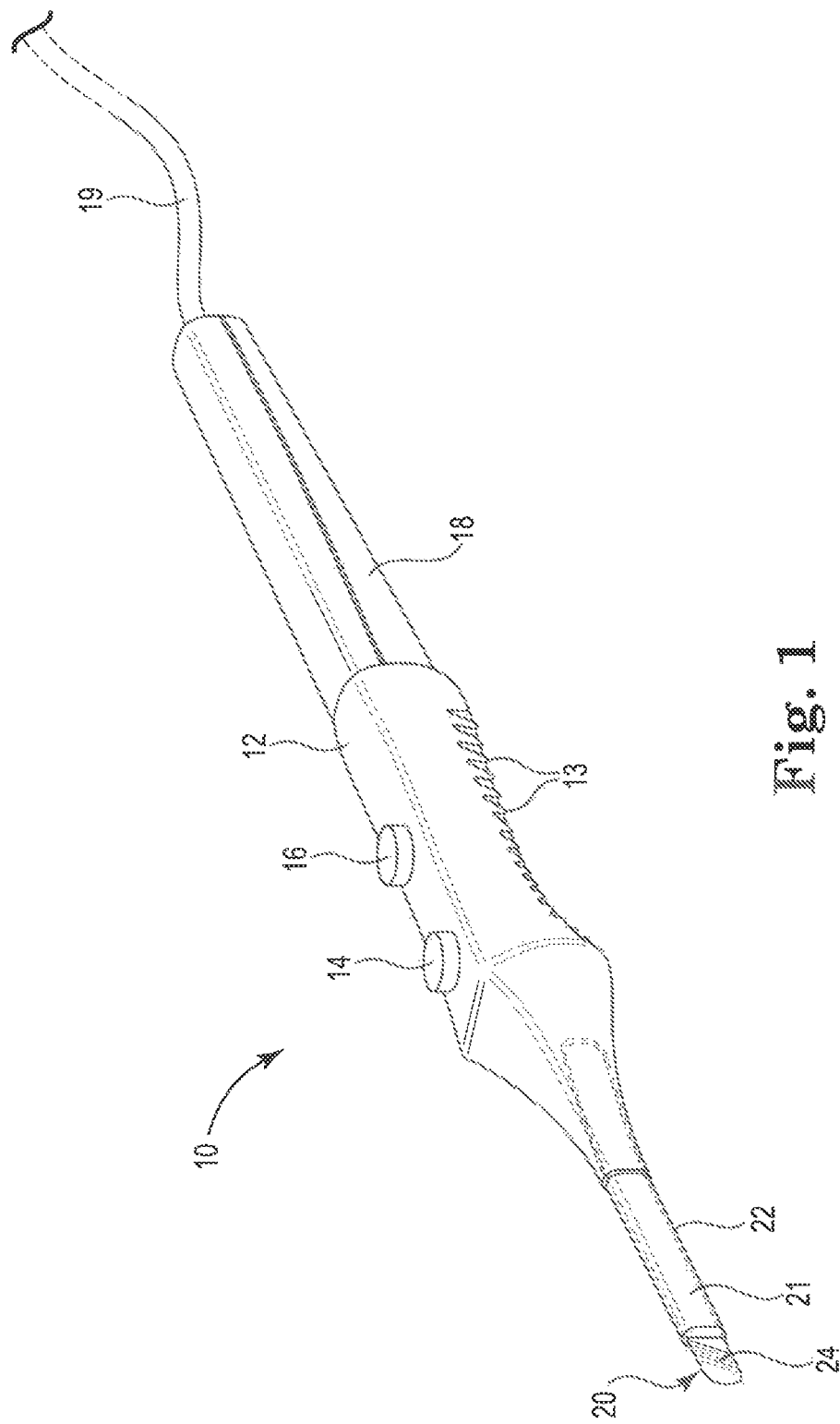
FIG. 1 is a perspective view of an electrosurgical cutting tool.

Unless otherwise specified, the following terms as used herein have the meanings provided below.

As used herein, "a," "an," "the," "at least one," and "one or more" are used interchangeably. Thus, for example, a coating composition that comprises "a" pigment can be interpreted to mean that the coating composition includes "one or more" pigments.

The term "amorphous" means a solid composition that lacks the order present in crystalline structures.

The terms "coefficient of thermal expansion" or "CTE" describes a thermomechanical property of a material and its ability to expand in size as the temperature is raised. For purposes of this disclosure, the CTE value is measured in accordance with ASTM E228-17, Standard Test Method for Linear Thermal Expansion of Solid Materials with a Push-Rod Dilatometer. The test heating rate is 5° C./min and the temperature range is from room temperature to about 1000° C. Those of ordinary skill in the art will recognize that the vitreous enamel is not tested after it is coated onto the metal electrode but rather the fired glass frit comprising the vitreous enamel is tested and corresponds to the CTE value of the vitreous enamel after coating and firing.

The terms "color" and "colored" mean having a hue (e.g., a primary color such red green or blue in an RGB additive color system, or a hue made by mixing two or more such primary colors) or a white coloration, but does not include a black coloration, The term "crystalline" refers to a solid material that possesses a highly ordered or arranged structure, may in some circumstances form a crystal lattice, and may in some circumstances be opaque.

The terms "electrosurgical cutting tool" or "electrosurgical cutting blade" generally refer to the electrosurgical equipment use of plasma energy to dissect tissue or coagulate blood vessels while producing minimal collateral damage to surrounding tissue.

The terms "enamel" or "vitreous enamel" describe a transparent, semitransparent or opaque glassy substance applied to metallic or other hard surfaces, and capable of serving as a dielectric or insulating layer for an electrosurgical cutting blade.

The term "glass-ceramic" refers to a vitreous enamel composition that includes both an amorphous phase and a crystalline phase.

The term "glass frit" means the basic materials, often in particulate form, that may be wholly fused, for making glass or vitreous enamel.

The term "metal substrate" refers the metal electrode of an electrosurgical cutting tool that forms the cutting blade and provides a base upon which the vitreous enamel is applied.

The term "opaque" refers to a glass that reflects rather than refracts light in a wavelength range of interest (typically but not in all cases the visible light range from 400 to 700 nm).

The terms "preferred" and "preferably" refer to embodiments of the invention that may afford certain benefits, under certain circumstances. However, other embodiments may also be preferred, under the same or other circumstances. Furthermore, the recitation of one or more preferred embodiments docs not imply that other embodiments are not useful, and is not intended to exclude other embodiments from the scope of the invention.

The recitation of numerical ranges by endpoints includes all numbers subsumed within that range (e.g., 1 to 5 includes 1, 1.5, 2, 2.75, 3, 3.80, 4, 5, etc.). Furthermore, disclosure of a range includes disclosure of all subranges included within the broader range (e.g., 1 to 5 discloses 1 to 4, 1.5 to 4.5, 1 to 2, etc.).

DETAILED DESCRIPTION

The disclosed vitreous enamel coating may be rendered diffusely reflective or absorptive in a variety of ways, and the disclosed reflective or absorptive characteristics may be broad-based across a variety of wavelengths (e.g., over the one or both of visible wavelength range of 400 to 700 nm and the infrared wavelength range of 700 nm to 1 mm) or may be selective over specific wavelengths of interest. In one relatively easily-implemented embodiment, the surface of the vitreous enamel coating may be etched or otherwise roughened so that it provides diffuse rather than specular reflection. The desired degree of surface roughness may be obtained using acidic or abrasive treatment of the coated electrosurgical blade. Caustic treatments may also be used but tend to be slower and thus are less preferred. Exemplary acidic treatments include exposure of the coated blade to suitable acid(s) such as hydrofluoric acid (HF), hexafluorosilicic acid ($H_2SiF_6$), or a mixture of acids and acid salts such as a mixture of HF and sodium fluoride (NaF) or a mixture of nitric acid ($HNO_3$), sulfuric acid ($H_2SO_4$) and ammonium bifluoride ($NH_4HF_2$). Exemplary abrasive treatments include sandblasting, abrasive disks and abrasive wheels. The desired degree of treatment may be assessed by evaluating the 60° gloss value using a BYK Micro-Tri-Gloss meter (Byk-Gardner, Inc.) and the procedures outlined in ASTM D523-14, Standard Test Method for Specular Gloss.

The disclosed vitreous enamel may also or instead be rendered diffusely reflective or absorptive by dispersing inorganic light-absorbing or light-reflecting pigment particles into the vitreous enamel. This may be done in a variety of ways, including adding the pigment particles to a glass fit from which the vitreous enamel will be prepared. In another embodiment, the pigment particles may be added to a slurry containing separately prepared milled glass particles together with a binder and optional solvent, followed by subjecting the slurry to a binder burnout step to remove the binder and optional solvent, followed by a firing step to form the vitreous enamel. The pigment particles desirably are more refractory than the glass so that they do not react with the glass during firing. At a sufficiently high loading level, the pigment particles may provide a highly dispersive or absorptive or even an opaque vitreous enamel. Black vitreous enamels or vitreous enamels having a variety of colors may be obtained. The desired degree of diffusely reflective or absorptive character may be evaluated using a gloss meter as discussed above.

Diffusely reflective or absorptive character may also be imparted to a vitreous enamel by adding to the glass frit one or more colorants (e.g., certain metal oxides) that become a part of the glass and cause absorption of energy in a wavelength range of interest (e.g., the visible light range). Without intending to be bound by theory, such absorption may facilitate transition of electrons from an unfilled d or f orbital of lower energy to one of higher energy upon exposure of the vitreous enamel to energy in the desired wavelength range. The desired degree of diffusely reflective or absorptive character may be evaluated using a gloss meter as discussed above.

Diffusely reflective or absorptive character may also be imparted to a vitreous enamel by selecting suitable frit ingredients or suitably processing the molten enamel so as to form a visibly distinct crystalline phase that scatters desired wavelengths of light (resulting for example in a colored black appearance), or a crystalline phase that scatters all wavelengths of visible light (resulting in a white or off-white appearance). The desired degree of crystallinity may be evaluated using a gloss meter as discussed above.

If desired, the various approaches outlined above may be combined. For example, two or more of etching or other roughening, addition of inorganic pigment particles, addition of colorants and imparting crystallization may be combined with one another to obtain the desired degree of diffusely reflective character, absorptive character or opacity.

FIG. 1 depicts an embodiment of an electrosurgical cutting device 10. Device 10 includes an insulated handle 12 with hand (e.g., finger) grip ridges 13 as shown on the lower part thereof. This portion is intended to be held in the surgeon's hand (not shown in FIG. 1). Two control buttons 14, 16 activate electric switches (not shown in FIG. 1) which are provided for respectively selecting cutting or coagulation regimes. The rear portion 18 is for balance and for housing at least one cable 19 that may terminate in a conventional electrical connector (not shown in FIG. 1) for connection to a lead, leads or mating connector of a radiofrequency energy power supply (not shown in FIG. 1). The dimensions of the device of FIG. 1 are such that it is comfortably held in a hand, yet small enough for surgery for the intended application. The working end of the device of FIG. 1 includes at its distal end an electrosurgical cutting blade 20. Electrosurgical cutting blade 20 includes a metal substrate or electrode 21 housed in an intermediate portion or shaft 22. Intermediate portion 22 provides an insulated support that holds and extends the distal end of electrosurgical cutting blade 20 at an appropriate surgical viewing and cutting or coagulating distance from the surgeon's hand. The exposed distal portion of electrosurgical cutting blade 20 includes a diffusely reflective or absorptive vitreous enamel insulative coating 24. A non-limiting embodiment of an exemplary electrosurgical device is disclosed in U.S. Pat. No. 8,414, 572 B2, herein incorporated by reference in its entirety.

As depicted in FIG. 1, device 10 has a single, flattened blade 20 fixedly mounted in intermediate portion 22. As will be appreciated by persons having ordinary skill in the art, the disclosed electrosurgical device may have a variety of other blade shapes and blade configurations, including blades with square edged, slant-edged, cylindrical, needle-like, bent, bendable or telescoping features. The disclosed electrosurgical device may be a monopolar device such as is shown in FIG. 1, or a bipolar device with two or more electrodes as may be used in some forms of electrosurgery.

In operation, the steps involved for cutting or otherwise operating on (e.g., coagulating) tissue with an electrosurgical device such as device 10 of FIG. 1 generally include contacting the tissue with a plasma generating electrode and applying an electric signal, having in some cases a low duty-cycle RF waveform, to the electrode. The signal causes the formation of a plasma discharge along the electrode between the electrode edge and the tissue and this plasma performs the tissue cutting or other operation.

The actual nature of the applied electrical signals which are suitable to create the desired plasma effect is well known in the field. For instance, in one embodiment the applied signal is an RF signal having a frequency in the range of 100 KHz to 10 MHz. Typically this energy is applied in the form of bursts of pulses. Each burst typically has a duration in the range of 10 microseconds to 1 millisecond. The individual pulses in each burst typically each have a duration of 0.1 to 10 microseconds with an interval therebetween of 0.1 to 10 microseconds. The actual pulses are typically square waves and bi-phasic, that is alternating positive and negative amplitudes. Generally the interval between pulses must be shorter than a lifetime of the plasma vapor cavity in order to maintain the cavity and the plasma regime during each pulse burst. In one embodiment the bursts are separated by a duration of at least one millisecond.

Figure 2:
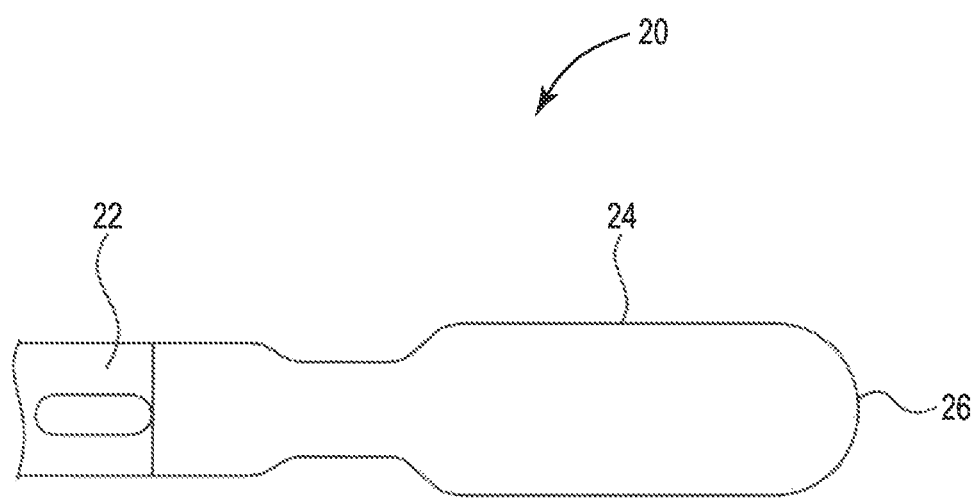
FIG. 2 is an orthogonal side view of a vitreous enamel-coated electrosurgical cutting blade.

The energy is delivered to the functional edge of the device through an electrosurgical cutting blade. FIG. 2 is an orthogonal side view of one embodiment of an electrosurgical cutting blade 20. The electrosurgical cutting blade 20 includes a metal electrode or substrate 22 at least a portion of which is coated with a diffusely reflective or absorptive vitreous enamel coating 24. An exposed edge 26 of the metal substrate 22, upon the introduction of radiofrequency energy, is capable of creating a substantially uniform and enhanced electrical field that upon contact with the cells in tissue forms the plasma medium. The vitreous enamel coating 24 functions as a non-conductive surface and thereby limits the formation of the plasma medium to the defined edge 26.

The chosen diffusely reflective or absorptive vitreous enamel coating can serve one or more of a variety of functions, including making the blade more visible against nearby tissue or nearby fluids, absorbing light emitted by a nearby plasma-mediated discharge, reducing second surface reflections from an underlying metal electrode substrate, reducing glare caused by specular reflection from the plasma mediated discharge or lights in the operating field, and discouraging reflection of visible or other light (e.g., infrared radiation) in colors that might interfere with markers, sensors or other instruments designed to measure light emitted by or passing through nearby tissue, e.g., by transillumination.

Figure 3:
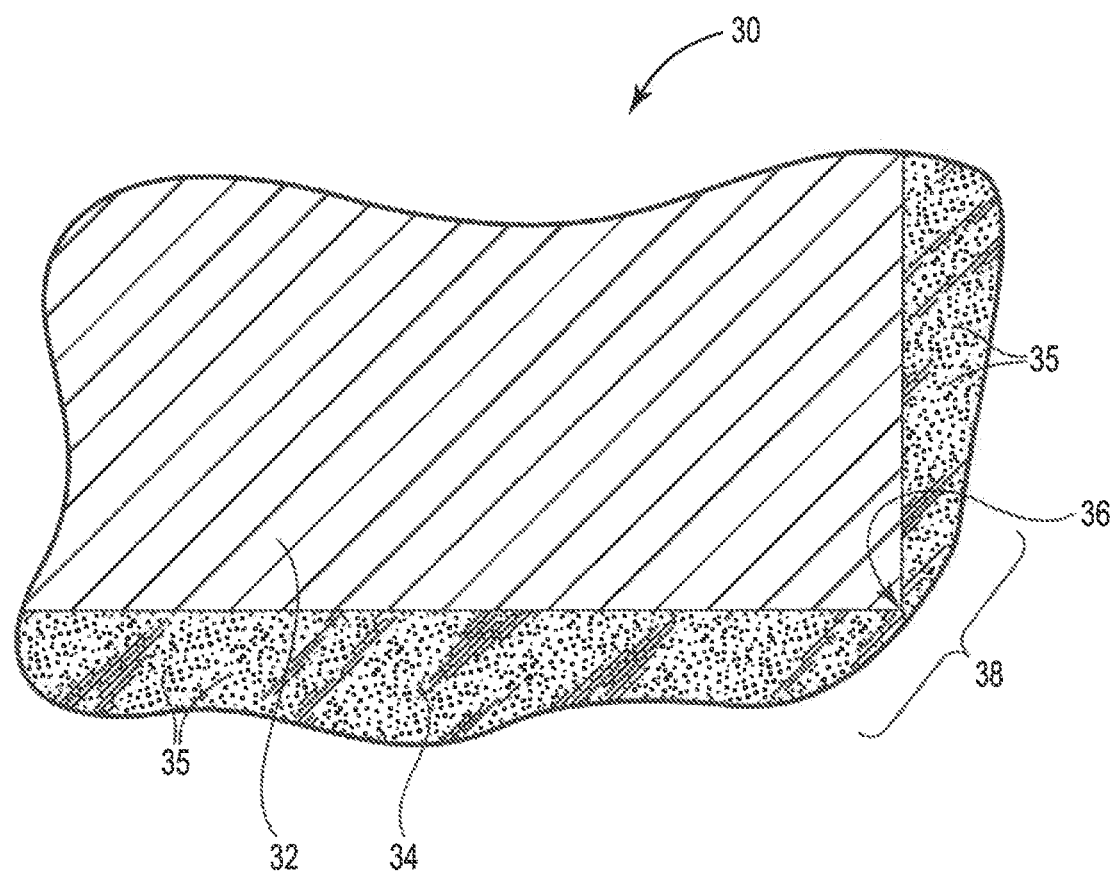
FIG. 3 is a cross-sectional schematic view of an edge portion of an electrosurgical cutting blade with a diffusely reflective or absorptive pigmented vitreous enamel coating.

FIG. 3 is a cross-sectional schematic view of an edge portion of a vitreous enamel-coated electrosurgical cutting blade 30. Blade 30 includes metal electrode substrate 32, diffusely reflective or absorptive vitreous enamel coating 34 optionally containing refractory inorganic oxide pigment particles 35, and edge 36. Coating 34 may be amorphous or crystalline, but has a sufficiently roughened surface in regions remote from edge 36 (imparted for example, using acid treatment, sandblasting or abrasion as discussed above), or contains sufficient particles 35, or is sufficiently roughened in such regions and contains sufficient inorganic particles, so that coating 34 is not specularly reflective in a wavelength or range of wavelengths of interest.

Due to surface tension and other factors during application or firing of the frit from which coating 34 is made, coating 34 typically will have a reduced thickness near edge 36. In some embodiments, edge 36 may be exposed following firing. If desired, a mechanical impact, abrasive, electrical energy, acid etching or other measures may be used to remove a portion of, or to discourage the formation of, coating 34 proximate edge 36, thereby resulting in a region with reduced thickness or no coating at all proximate edge 36. Such reduced thickness or exposed edge provides a localized reduction in the breakdown voltage strength of coating 36, helps promotes initial plasma formation and plasma maintenance proximate edge 36 when electromagnetic energy is applied to metal electrode 32, and is in addition to the roughening discussed above in regions of blade 30 remote from edge 36.

In a preferred embodiment, coating 34 is sufficiently roughened in regions remote from edge 36, or sufficiently pigmented, so that substrate 32 is not visible through portions of coating 34 that are remote from edge 36 (viz., portions that are not adjacent to edge 36 and consequently do not have a reduced thickness) under normal indoor illumination. In another further preferred embodiment, coating 34 contains sufficient pigment particles 35 so that substrate 32 is not visible through such remote portions of coating 34 under the illumination provided by the plasma mediated discharge or under typical operating theater illumination. Coating 34 consequently preferably reduces or eliminates unwanted second surface specular reflection of light traveling through (viz., into and out of) coating 34. Such light is instead preferentially scattered or absorbed (e.g., via diffuse reflection) by the roughened surface of coating 34 or by the optional pigment particles 35.

The disclosed second surface reflection may also be reduced or eliminated by altering the light-handling characteristics of the interface between coating 34 and metal substrate 32. This may for example be done by etching or otherwise roughening metal substrate 32 in regions remote from edge 36 using mechanical impact, abrasive, electrical energy, acid etching as described above, using techniques that will be familiar to persons having ordinary skill in the metalworking art. Acid etching is a preferred approach and on stainless steel blade substrates may for example be performed using hydrochloric acid (HCl), nitric acid or sulfuric acid (H2SO4), optionally together with salts such as ferric chloride ($FeCl_3$) or copper sulfate ($CuSO_4$).

Figure 4:
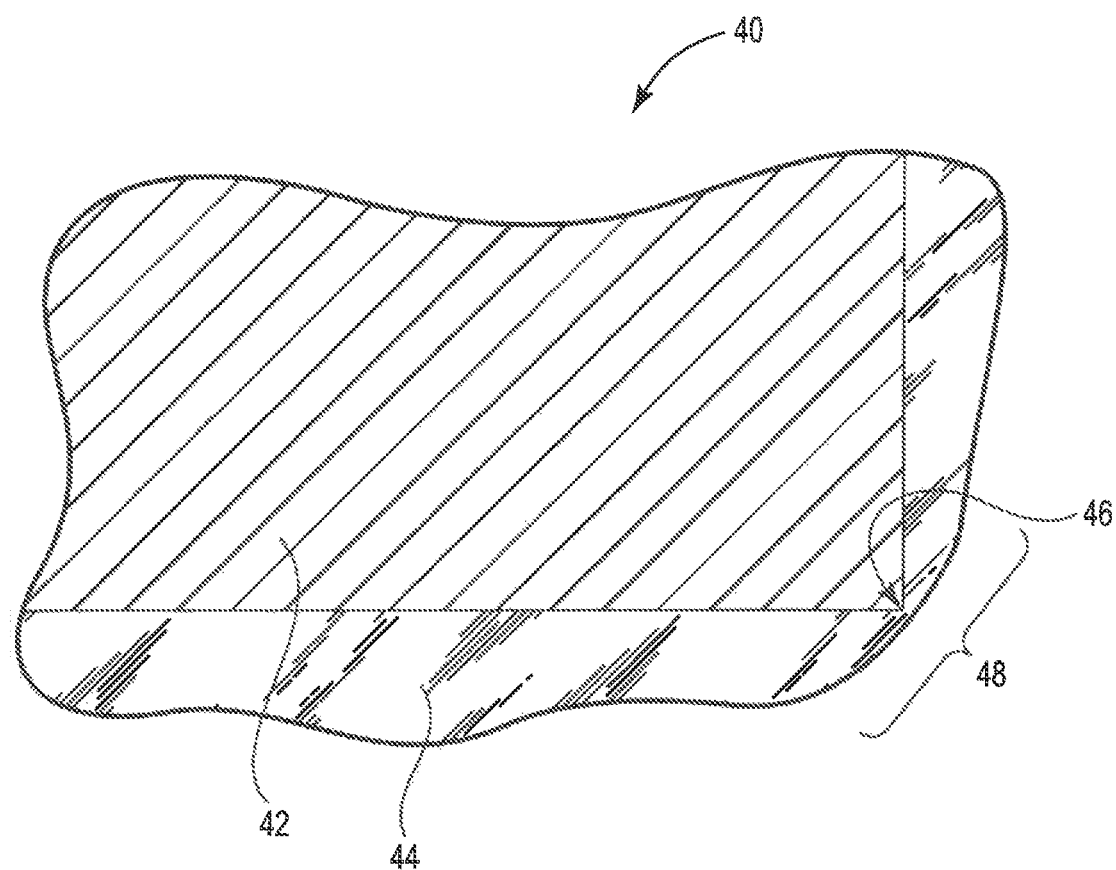
FIG. 4 is a cross-sectional schematic view of an edge portion of an electrosurgical cutting blade with a diffusely reflective or absorptive crystalline vitreous enamel coating.

FIG. 4 is a cross-sectional schematic view of an edge portion of a vitreous enamel-coated electrosurgical cutting blade 40. Blade 40 includes metal electrode substrate 42, diffusely reflective or absorptive vitreous enamel coating 44, and edge 46. Blade 40 is similar to blade 30 in FIG. 3. Coating 44 contains diffusely reflective or absorptive character due to one or more measures. Such measures may include addition to the glass frit from which coating 44 is made of colorants (e.g., certain metal oxides) that become a part of the glass and cause absorption of energy in a wavelength range of interest (e.g., the visible light range). Such measures may also include processing the vitreous enamel so that coating 44 has appreciable crystallinity and scatters or absorbs desired wavelengths of light, resulting in a colored appearance, or scatters all wavelengths of visible light, resulting in a white or off-white colored appearance. In a preferred embodiment, coating 44 is made from sufficient such colorants or contains sufficient crystallinity so that substrate 42 is not visible through portions of coating 44 that are remote from edge 46 under normal indoor illumination. In another further preferred embodiment, coating 44 is made from sufficient such colorants or contains sufficient crystallinity so that substrate 42 is not visible through such remote portions of coating 44 under the illumination provided by the plasma mediated discharge or under typical operating theater illumination. The colorants or crystallinity in coating 44 consequently preferably reduce or eliminate unwanted second surface specular reflection of light traveling through (viz., into and out of) coating 44. Such light is instead preferentially absorbed or scattered (e.g., via diffuse reflection) by the presence of one or both of colorant(s) or crystalline phase(s) within coating 44.

If desired, coating 44 or substrate 42 may also be roughened as discussed above in connection with FIG. 3, or coating 44 may contain optional refractory inorganic pigment particles like the particles 35 in FIG. 3 (not shown in FIG. 4). This can help provide further diffusely reflective or absorptive character to coating 44 and blade 40.

Figure 5:
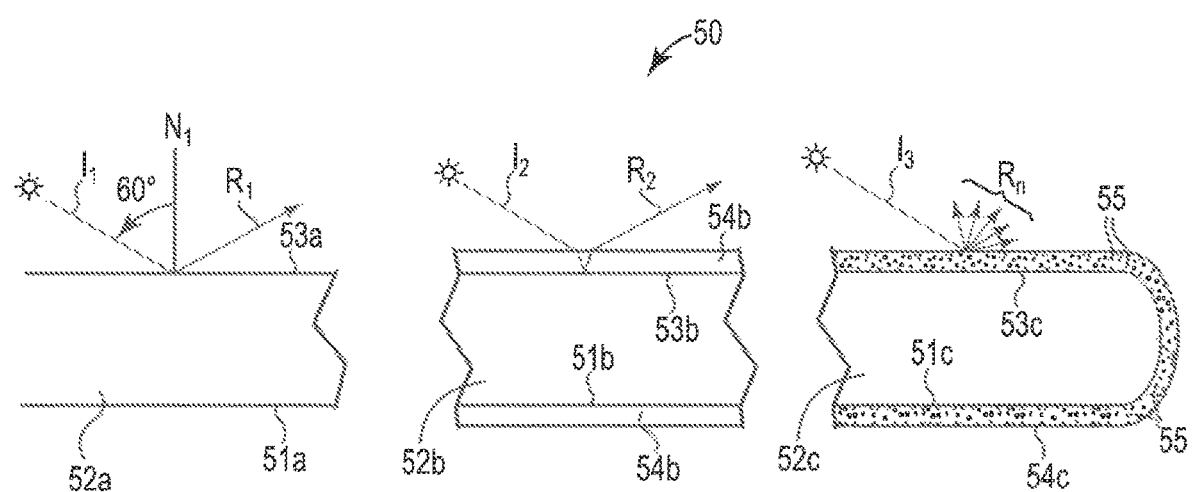
FIG. 5 is a cross-sectional schematic view of a portion of a coated electrosurgical cutting blade illustrating specular and diffuse reflection.

FIG. 5 is a cross-sectional schematic view of three portions of a coated electrosurgical cutting blade 50. Blade 50 is shown on the left of FIG. 5 with an uncoated metal substrate portion 52a having exposed upper and lower metal surfaces 51a and 53a, respectively; in the center of FIG. 5 with a coated metal substrate portion 52b having on its lower surface 51b and upper surface 53b an unfilled, transparent or translucent, smooth-surfaced layer of vitreous enamel coating 54b; and on the right of FIG. 5 with metal substrate portion 52c having on its lower surface 51c and upper surface 53c a layer of vitreous enamel coating 54c that is made diffusely reflective using one or more of the measures described above. Different coatings are thus shown on substrate portions 52b and 52c. In a typical vitreous enamel coated electrosurgical blade, there may be an uncoated distal section like portion 52a, and a proximal portion bearing a vitreous enamel coating. Often the coating will be the same throughout, but this is not required. Different coatings, or coatings having differing degrees of reflectivity or absorptivity, may be used on different portions of the blade. For example, in an asymmetric blade having a single sharpened edge, a distinctive diffusely reflective or absorptive coating may be applied to regions remote from the edge, and a transparent coating may be applied to a region encompassing the edge, so as to assist the surgeon in readily identifying the edge location.

Incident light ray $I_1$ is shown striking the upper surface 53a of substrate portion 52a at a 60° angle with respect to perpendicular (normal) dashed line $N_1$, and undergoing specular reflection as reflected ray $R_1$ travelling away from upper surface 53a at a similar 60° angle. Because the surface of a traditional electrosurgical cutting blade is typically ground flat and may be highly polished, the reflected ray $R_1$ will typically be nearly as intense and nearly as focused as incident ray $I_1$.

Incident light ray $I_2$ is shown striking the upper surface of vitreous enamel coating 54b on substrate portion 52b at a 60° angle, undergoing refraction through coating 54b, striking and being specularly reflected away from upper surface 53b, passing back through coating 54b and emerging at a 60° angle from the upper surface of coating 54b as specular reflected light ray $R_2$. As was the case for rays $I_1$ and $R_1$, reflected ray $R_2$ may be nearly as intense and nearly as focused as incident ray $I_2$.

Incident light ray $I_3$ is shown striking the upper surface of vitreous enamel coating 54c on substrate portion 52c at a 60° angle. Due to surface roughening of coating 54c, the presence of refractory inorganic pigment particles 55 or crystallinity in coating 54c, or other measures discussed above, incident ray $I_3$ is diffusely reflected away from coating 54c as reflected rays $R_n$. Reflected rays $R_n$ will present a less intense, unfocused appearance and exhibit much less glare than reflected rays $R_2$ and $R_3$.

The disclosed electrosurgical cutting blade includes a metal electrode that provides electrical connectivity to the power source and offers (or may be altered to offer) an exposed edge to enable the formation of plasma. Non-limiting examples of metals suitable to form electrodes include titanium, tantalum, molybdenum, tungsten, stainless steel, or alloys thereof. In some embodiments, the metal electrode can be cut or stamped from metal substrates. Secondary process steps such as etching, grinding or polishing may also be used on blades intended for use in certain surgical applications. The dimensions and shape of the metal electrode may also vary to accommodate different surgical applications. The metal electrode in some preferred embodiments possesses a CTE value from about 6, 8 or $10\times10^{-6}/°$ C. up to about 11, 12, or $16\times10^{-6}/°$ C.

The vitreous enamel may comprise a variety of glass or glass-ceramic materials. The selection of suitable glass or glass-ceramic materials will depend on several factors including, but not limited to, the end use surgical application, nearby illumination, blade design, expected temperatures during plasma formation, power voltage of the RF generator, water content of the tissue, and nature and extent of bonding to the metal substrate. In certain aspects, the glass or glass-ceramic composition may be selected to achieve a softening temperature that is near or preferably above the temperatures realized during plasma formation. For example, the softening temperature of a glass or glass-ceramic composition may be at least 500° C., at least 600° C. or at least 700° C. A softening temperature of at least 500° C. may in some circumstances enhance the durability of the glass. By increasing the softening temperature, the glass may withstand higher temperatures without softening and flowing during use.

The vitreous enamel may be created through the combination of various compounds to form certain types of glass. One embodiment includes the formation of an aluminoborosilicate glass with at least $SiO_2$, $B_2O_3$ and $Al_2O_3$ compounds. In a preferred aluminoborosilicate glass embodiment, the glass frit includes one or more alkaline earth oxides. Preferred such alkaline earth oxides include magnesium oxide (MgO), calcium oxide (CaO), strontium oxide (SrO) and barium oxide (BaO). Higher molecular weight alkaline earth oxides tend to provide higher CTE values. SrO is an especially preferred alkaline earth oxide for use in the disclosed aluminoborosilicate glasses.

As mentioned above, a variety of refractive inorganic pigments may be added to the disclosed vitreous enamel to provide diffusely reflective or absorptive character, and in preferred embodiments an opaque coating. Exemplary such pigments include materials that may be classified as ceramic or refractory pigments, and which may contain elements such as cobalt (Co), chromium (Cr), copper (Cu), iron (Fe) and manganese (Mn). Exemplary commercially available pigments include BAYFERROX™, BAYOXIDE™, COLORTHERM™ and LANXESS™ pigments from BASF, titanium dioxide pigments from DowDuPont, chromic oxide pigments from Elementis, phosphate ceramics from the ICL Group, and mineral-based pigments from Prince Minerals GmbH. The chosen pigment should be biocompatible, and consequently should avoid the use of potentially toxic metals (e.g., lead, cadmium and other materials that will be familiar to persons having ordinary skill in the art) and their oxides. In a preferred embodiment, the pigment is a non-infrared absorptive pigment. Exemplary such pigments include single or mixed metal oxides formed from a variety of metals, e.g., from aluminum, antimony, bismuth, boron, chromium, cobalt, gallium, indium, iron, lanthanum, lithium, magnesium, manganese, molybdenum, neodymium, nickel, niobium, silicon, tin, titanium, vanadium or zinc. Exemplary metal oxides include $Cr_2O_3$, $Al_2O_3$, $V_2O_3$, $Ga_2O_3$, $Fe_2O_3$, $Mn_2O_3$, $TiO_2$, $Ti_2O_3$, $In_2O_3$, $TiBO_3$, $NiTiO_3$, $MgTiO_3$, $CoTiO_3$, $ZnTiO_3$, $FeTiO_3$, $MnTiO_3$, $CrBO_3$, $NiCrO_3$, $FeBO_3$, $FeMoO_3$, $FeSn(BO_3)_2$, $BiFeO_3$, $AlBO_3$, $Mg_3Al_2Si_3O_{12}$, $NdAlO_3$, $LaAlO_3$, $MnSnO_3$, $LiNbO_3$, $LaCoO_3$, $MgSiO_3$, $ZnSiO_3$ and $Mn(Sb, Fe)O_3$. The metal oxide may have a corundum-hematite crystal lattice structure as described in U.S. Pat. No. 6,454,848 B2, or may be a host component having a corundum-hematite crystalline structure which contains as a guest component one or more elements selected from aluminum, antimony, bismuth, boron, chromium, cobalt, gallium, indium, iron, lanthanum, lithium, magnesium, manganese, molybdenum, neodymium, nickel, niobium, silicon, tin, vanadium and zinc. A variety of non-infrared-absorptive pigments are commercially available, including mixed metal oxide pigments such as those supplied by Ferro Corporation (Cleveland, OH) under the COOL COLORS™ and ECLIPSE™ trademarks, for example V-778 COOL COLORS IR Black, V-780 COOL COLORS IR Black, V-799 COOL COLORS IR Black, 10201 ECLIPSE Black, 10202 ECLIPSE Black and 10203 ECLIPSE Black; mixed metal oxide pigments such as those supplied by Shepherd Color Company (Cincinnati, OH) under the ARTIC™ trademark, for example ARTIC Black 376, ARTIC Black 10C909, ARTIC Black 411 and ARTIC Black 30C940; and mixed metal oxide pigments such as those supplied by Tomatec America, Inc. (Florence, KY) under the numbers 42-707A and 707V10. The selection of a particular pigment may depend in part upon the softening temperature of the vitreous enamel and the heat stability of the individual pigment. Not all pigments will have sufficient heat resistance to be used with all glass frits or with all glass powder firing steps. Sufficient pigment should be used to provide the desired degree of light scattering or absorption while maintaining adequate processability and final properties in the vitreous enamel. Based on the final weight of the vitreous enamel, the vitreous enamel may for example contain at least about 0.1, at least about 0.2, at least about 0.5, at least about 1, at least about 5 or at least about 10 weight % pigment, and up to about 50, up to about 40, up to about 30 or up to about 20 weight % pigment.

As mentioned above, one or more colorants that become a part of the glass and cause absorption of energy in a wavelength range of interest may be added to the glass frit to provide light absorption, and in preferred embodiments an opaque coating in the final vitreous enamel. A variety of such colorants may be employed, and will be familiar to persons having ordinary skill in the glassmaking art. Exemplary colorants include many transition metals and lanthanides and their oxides. For example, $Co^{2+}$ ion absorbs light at wavelengths of about 500 to 700 nm and reflects blue light. Consequently, addition of cobalt oxide to the frit will impart a blue coloration to the vitreous enamel. Iron(II) oxide or chromium oxide may be employed to obtain bluish-green or green coloration. In borosilicate glasses rich in boron, sulfur imparts a blue color, and with calcium yields a deep yellow color. Manganese can be added to provide an amethyst or violet coloration, especially in the presence of sodium via formation of sodium permanganate. Copper oxide may be employed to obtain turquoise coloration. Nickel oxides may be used at various concentrations to obtain blue, violet, or black glass. Chromium oxide may be employed to obtain dark green or black coloration. Sufficient colorant should be used to provide the desired degree of light absorption while maintaining adequate frit processability. Based on the final weight of the vitreous enamel, the vitreous enamel may for example contain at least about 0.1, at least about 0.2, at least about 0.5 or at least about 1 weight % colorant, and up to about 30, up to about 20, up to about 10 or up to about 5 weight % colorant.

As mentioned above, diffusely reflective or absorptive character may also be imparted to a vitreous enamel by selecting suitable frit ingredients or suitably processing the molten enamel so as to form a visibly distinct crystalline phase that scatters all wavelengths of light, resulting in a white or off-white colored appearance. If diffusely reflective or absorptive character is imparted to the vitreous enamel using other measures such as surface roughing, pigments or colorants as discussed above, then crystallinity is not necessary and the vitreous enamel composition may be an amorphous glass. However, in other embodiments the vitreous enamel composition includes a crystalline phase or additives that represent a crystalline phase. For example, the vitreous enamel may include a glass-ceramic composition. Glass-ceramic compositions may possess a crystalline phase along with the amorphous glass. The crystallinity of the vitreous enamel upon firing and formation may beneficially enhance the opacity and light-scattering or absorption behavior of the vitreous enamel. Non-limiting examples of crystalline phases include $Ca_2ZnSi_2O_7$ (hardystonite) or $Sr_2SiO_4$. Other combinations of compounds, such as nucleating agents, may be included in a glass frit and fired to create a glass-ceramic composition with at least a partial crystallinity that beneficially impacts the thermomechanical properties of the vitreous enamel-coated electrosurgical cutting blade. Crystallinity may also be imparted by adding to the glass frit one or more separate crystalline glass additives such as SIL-CEL™ 43 glass micro cellular fillers (from Silbrico Corporation, Hodkins, IL), FILLITE™ 100 ceramic spherical particles (from Trelleborg Fillite Inc., Norcross, GA), SPHERICEL™ hollow glass spheres (from Potter Industries Inc., Valley Forge, PA), 3M ceramic microspheres including grades G-200, G-400, G-600, G-800, W-210, W-410, and W-610 (from 3M. St. Paul, MN) or 3M hollow microspheres including 3M Performance Additives iM30K (also from 3M). Not all such crystalline glass additives will have sufficient heat resistance to be used with all glass frits. Sufficient crystallinity should be imparted to the vitreous enamel, or sufficient crystalline glass additive should be added to the glass frit, to provide the desired degree of diffusely reflective or absorptive character while maintaining adequate frit processability. When a crystalline glass additive is employed, and based on the final weight of the vitreous enamel, the vitreous enamel may for example contain at least about 0.1, at least about 0.2, at least about 0.5, at least about 1, at least about 5 or at least about 10 weight % crystalline glass additive, and up to about 50, up to about 40, up to about 30 or up to about 20 weight % crystalline glass additive. Expressed on a volume basis, the glass used to prepare the vitreous enamel preferably contains at least about 10, at least about 15, at least about 20, at least about 30, at least about 40, at least about 50 or at least about 60 volume percent crystalline phase(s).

The chosen glass compositions may include other compounds to impart or enhance certain features or characteristics such as glass transition temperature (Tg), nucleation, water resistance, diffuse reflection characteristics, CTE and dielectric properties. For example, the glass may include additives to impart to the glass a desired CTE or ingredients to impart distinctive coloration. Exemplary and non-limiting examples of other compounds that may be components of a glass frit to form the vitreous enamel include the alkaline earth oxides mentioned above, zinc oxide, magnesium oxide, sodium oxide, and potassium oxide. Such compounds may optionally be included in the glass frit at molar percentages ranging on a molar percentage from a trace, 0.1%, 1%, 2%, 5% or 10% up to about 5%, 10%, 15% 20%, 30% or 40%. The frit desirably excludes materials that would not be biocompatible, for example lead or other toxic metals and their oxides. Exemplary glass frits and glasses include those from suppliers such as Elan Technology, Ferro Corporation, Mo-Sci Corporation and Schott AG. In a preferred embodiment, and before taking into account the addition of refractory pigments, colorants or crystalline glass additives as discussed above, a glass frit having the following compounds and molar percentages may be well suited for forming a vitreous enamel on an electrosurgical cutting blade: $SiO_2$ 30-50%, $B_2O_3$ 0.5-15%, $Al_2O_3$ 0.5-10%, SrO 5-30%, CaO 5-30%, and ZnO 0.5-20%.

Without being bound by theory, it is believed that the components in the disclosed vitreous enamel frit and vitreous enamel coating offer various attributes. For example, the function of each component in the glass composition may provide or offer certain features to the resulting enamel The $Si_2O$ helps form the glass network. Modifiers such as alkali and alkaline earth oxides may increase the CTE value and potentially decrease the glass transition temperature. $Al_2O_3$ may modify the crystallization rate. Minor additives such as $TiO_2$ and $ZrO_2$ may act as nucleating agents. $B_2O_3$ may modify the extent and rate of crystallization and improve wetting of the glass to the metal substrate. $B_2O_3$ may also increase the vitreous enamel CTE. High CTE partially crystallizing systems may for example also include one or both of SrO and BaO. In some embodiments the vitreous enamel has a CTE of about $6\times10^{-6}/°$ C. to about $16\times10^{-6}/°$ C. and more preferably about $10\times10^{-6}/°$ C. to about $12\times10^{-6}/°$ C. The dielectric strength of the vitreous enamel coatings may vary and in preferred embodiments may be greater than about 20,000, about 30,000 or about 40,000 volts/mm (about 508, about 762 or about 1016 volts/mil) as measured using ASTM D149-09.

Figure 6:
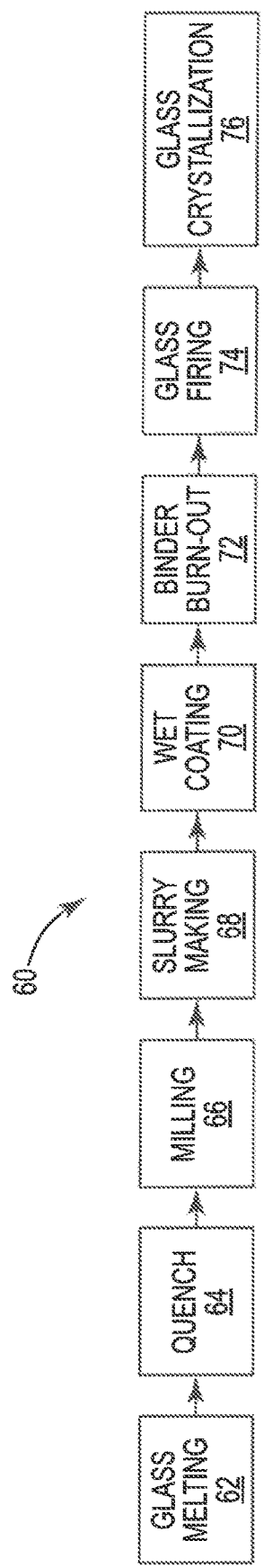
FIG. 6 is a schematic of one embodiment of a process for forming a vitreous enamel coating on an electrosurgical cutting blade.

FIG. 6 is an illustration of one embodiment of a process 60 suitable for forming a vitreous enamel coating on an electrosurgical cutting blade from a glass frit. The fit may be separately-supplied or may be manually prepared just prior to use. Glass inciting step 62 is typically performed by mixing and melting the frit components (including any refractory pigments, colorants or crystalline glass additives) in a furnace and quenching 64 the melt to form a solidified glass material. The resulting glass material is then milled 66 to a desired particle size that will support coating and formation of a vitreous enamel on the metal substrate. Those of ordinary skill in the art will recognize that particle size may have an impact on the properties of the resulting vitreous enamel. In certain embodiments, the particles may have a $d_{90}$ value between about 20 and about 50 μm (viz., 90 vol. % of the particles may in such embodiments have an average diameter below about 20 to below about 50 μm). In an optional wet coating step, a slimy 68 is prepared to facilitate the coating 70 of glass powder onto the metal substrate. The slurry may for example be prepared by dispersing the glass particles in a binder and carrier. The carrier can be any suitable solvent that is capable of maintaining a stable dispersion and a suitable viscosity for coating. Non-limiting examples of suitable carriers include mineral oil, ethanol, terpineol or combinations thereof. The binder enhances wet out and coating of the metal substrate during the coating process. Non-limiting examples of suitable binders include polyvinyl butyral, polyvinyl alcohol, and ethyl cellulose. Alternatively, the coating may be applied using a dry coating process, thereby alleviating the need for slurry formation. In any event, a variety of coating processes 70 may be employed. Non-limiting examples include electrophoretic deposition, dip coating, roll coating, spray coating or other similar application processes. The coating is preferably applied at a thickness sufficient to obtain a vitreous enamel coating that, after firing, will not unduly degrade during plasma formation and preferably will not suffer the defects that arise when using conventional vitreous enamel coatings. In a preferred embodiment, the metal substrate is coated to a vitreous achieve enamel coating thickness of about 50 μm to about 100 μm. In certain aspects in wet coating processes, the viscosity of the slurry may be controlled to address the coating thickness. Additionally, the coating is preferably applied in a manner that provides an exposed or only thinly-coated cutting edge. The edge may as discussed in connection with FIG. 3 be manually exposed by removing a portion of the vitreous enamel coating. The selection of a particular coating process may be dependent on various factors, including the metal substrate, the size and geometry of the cutting blade, and the type of glass frit, among others. Those of ordinary skill in the art will be capable of matching a particular coating process to achieve a desired enamel thickness on an electrosurgical cutting blade.

When using the slurry making step 68 and wet coating step 70 shown in FIG. 6, the binder and solvent are typically removed in a binder burn-out step 72. The electrosurgical cutting blade may be heated to a temperature and for a time sufficient to drive off any binder and solvent from the glass powder. The duration and temperature for this process may vary depending on the solvent or binder composition. In some embodiments, the temperature ranges up to about 500° C. for a time up to about 60 minutes. After this process, the remaining coating has green strength and ready for glass firing to form a vitreous enamel.

The glass firing process 74 encompasses ramping up the furnace temperature to the glass's firing temperature for a limited time to form the vitreous enamel, fuse it to the substrate, and anneal the final coating. Optionally, certain embodiments may allow for the formation of a crystalline phase 76. The firing generally takes place above 700° C. and in some embodiments above 750° C., or even above 800° C. The duration of the firing process and the time the coated substrate is held at temperature may for example vary depending upon the glass composition, coating thickness, type of metal substrate, blade shape and size, and other factors. Additionally, the let-down temperature may vary and may be staggered to enable solidification, annealing and stress relief. In certain embodiments, the annealing temperature is established at or above the Tg value for the selected vitreous enamel composition. The resulting vitreous enamel-coated electrosurgical cutting blade may for example be very similar in appearance to the embodiment shown in FIG. 2.

EXAMPLES

Example 1

Etched Blades

Vitreous enamel coatings on electrosurgical blades were prepared by combining ground glass, a solvent and dispersant in the amounts shown below in Table 1. The resulting mixtures were ball milled for about two hours to ensure an appropriate level of dispersion. The binder amount shown in Table 1 was added to the mixture and ball milled for about 4 hours to create a slurry. The viscosity of each slurry was measured using a Brookfield DV2T (LV) viscometer and spindle SC4-18/13R, and maintained above 1500 cp at 0.2 rpm. Each slurry was applied onto 420 stainless steel electrosurgical cutting blades using a dipping process. After the slurry coating was applied, the coated blades were subjected to burnout at about 600° C. for more than 60 minutes and subsequent firing at a temperature greater than 800° C. for more than 10 minutes. Upon the slow ramp down of the temperature to room temperature, the vitreous enamel-coated electrosurgical blades were visually inspected and found to have well-adhered, smooth, glossy vitreous enamel coatings with a 60° gloss rating greater than 105 gloss units.

TABLE 1

| Ingredient | wt. % |
| --- | --- |
| Sr—Ca—Zn—Al—B—Si alkaline earth aluminoborosilicate glass powder | 58 |
| Toluene/ethanol solvent mixture | 17 |
| Triethyl phosphate dispersant | 1.2 |
| Ethyl cellulose binder | 23.8 |
| Total | 100 |

Some of the coated blades were set aside as a control. The vitreous enamel surface of other coated blades was etched by immersing the coated blades for 2 to 5 seconds into the tri-acid etchant composition shown below in Table 2, followed by rinsing the blades with deionized water for 2 minutes and drying the blades using either compressed air or a 10 minute bake in an 80° C. drying oven.

TABLE 2

| Tri-Acid Etchant | |
| --- | --- |
| Ingredient | Concentration |
| Nitric acid | 50 vol. % |
| Sulfuric acid | 15 vol. % |
| Ammonium bifluoride ($NH_4HF_2$) | 120 g/L |
| Deionized water | 35 vol. % |

Figure 7:
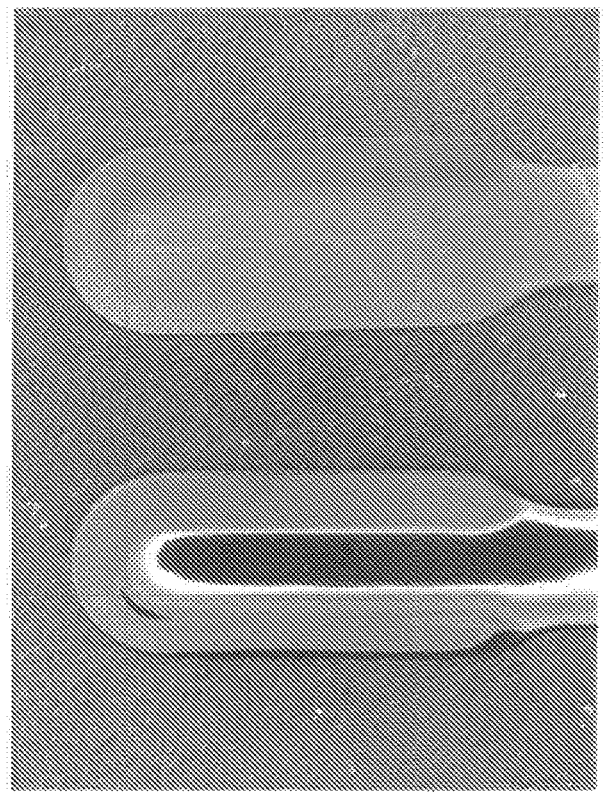
FIG. 7 is a photograph of electrosurgical blades bearing unetched or etched vitreous enamel coatings prepared in Example 1 and exhibiting different surface gloss.
Figure 8:
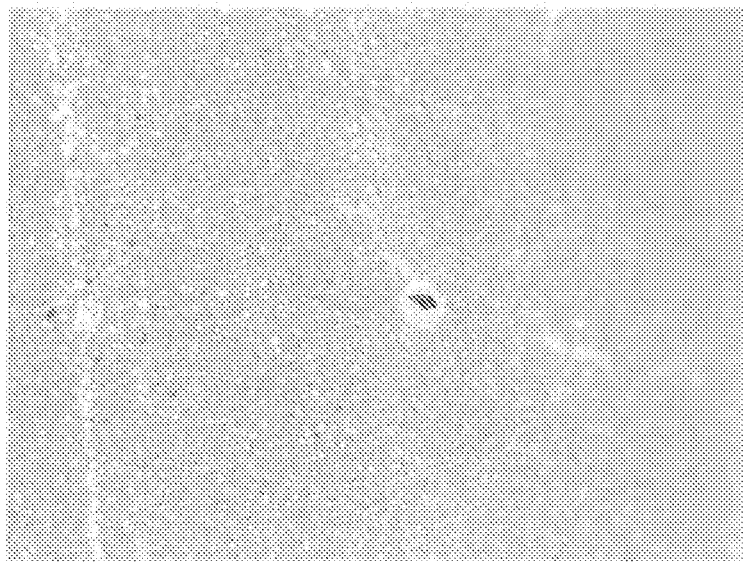
FIG. 8 is a photomicrograph of the etched vitreous enamel coating prepared in Example 1.
Figure 9:
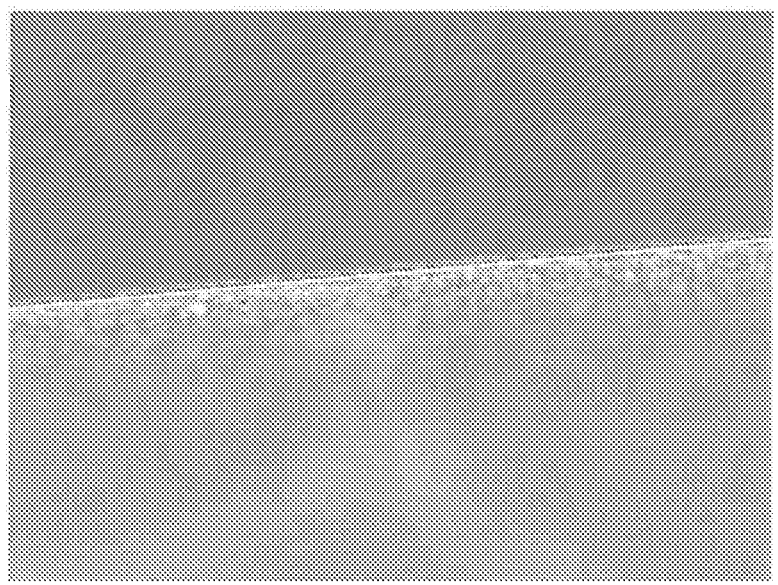
FIG. 9 is a photomicrograph of the blade edge for the etched coated electrosurgical blade prepared in Example 1.

A control blade and a blade etched for two seconds are shown side-by-side in FIG. 7. The etchant reacted with the glass, resulting in a roughened, diffusely reflective and glare-free visible surface with noticeably less surface gloss than the control blade. A photomicrograph of the etched surface is shown in FIG. 8, and a photomicrograph of the blade edge is shown in FIG. 9. A thin layer of the vitreous enamel coating remained on the blade edge and was not removed by the etching procedure.

Example 2

Crystalline Vitreous Enamel

Vitreous enamel coated electrosurgery blades like the control blades described in Example 1 were subjected to controlled heat treatment at four different temperatures. The heat treatments, volume % crystallinity and 60° gloss measurements are shown below in Table 3:

TABLE 3

| Heat Treatments to Induce Crystallinity | | |
| --- | --- | --- |
| Heat Treatment | Vol. % Crystallinity | Gloss at 60° Illumination, Gloss Units |
| 800° C. hold for 15 min | 1.1 ± 0.4 | 108.7 ± 0.6 |
| 830° C. hold for 15 min | 8.5 ± 1.5 | 106.7 ± 0.6 |
| 850° C. hold for 15 min | 23.3 ± 3.1 | 51.9 ± 5.6 |
| 870° C. hold for 15 min | 65 ± 15 | 7.4 ± 0.7 |

Figure 10:
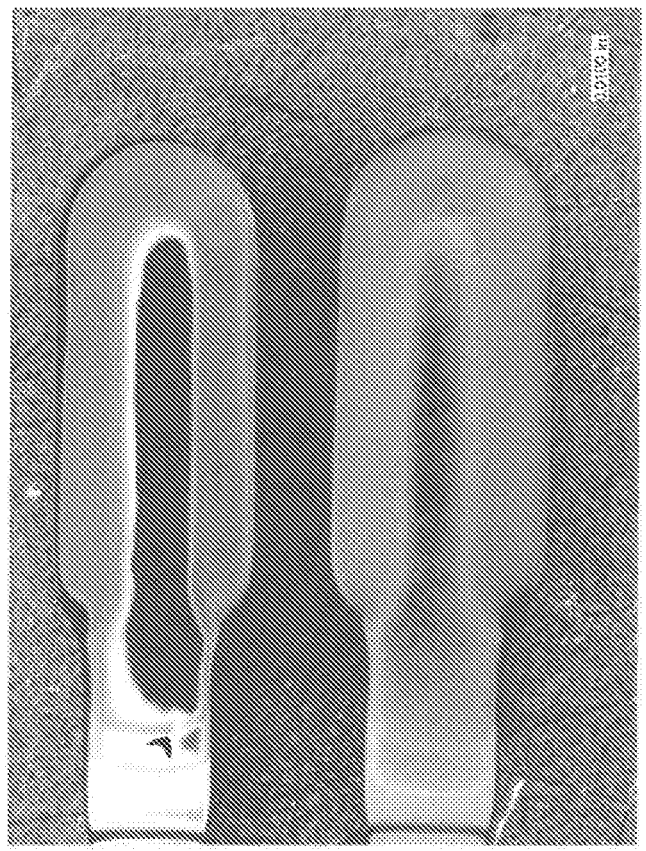
FIG. 10 is a photograph of electrosurgical blades prepared in Example 2, heat treated to two different final temperatures and exhibiting different surface gloss and crystallinity.
Figure 11:
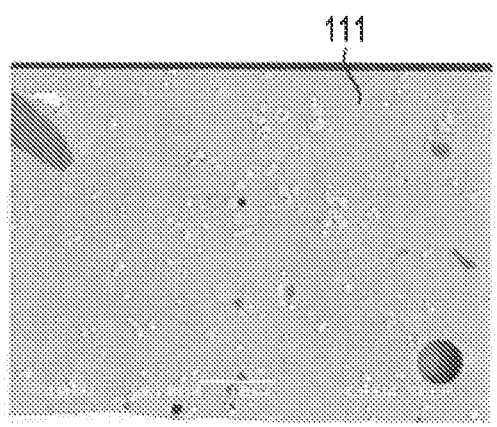
FIG. 11 through FIG. 14 are photomicrographs of four heat-treated vitreous enamels prepared in Example 2.
Figure 12:
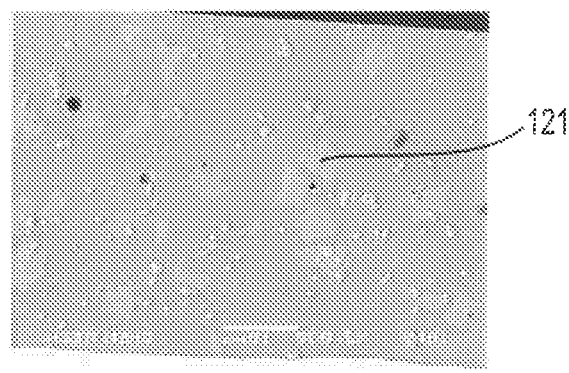
Figure 13:
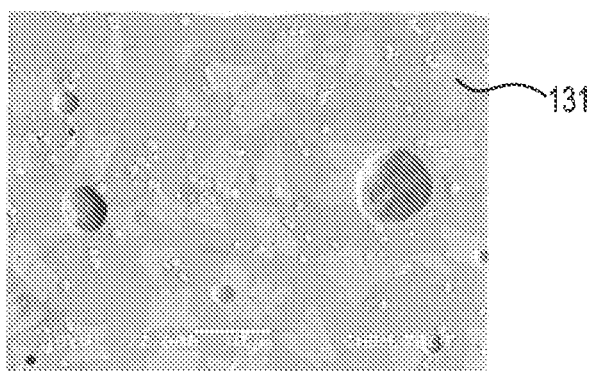
Figure 14:
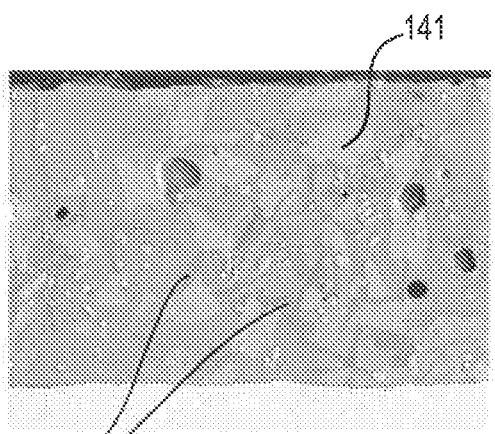
Figure 15:
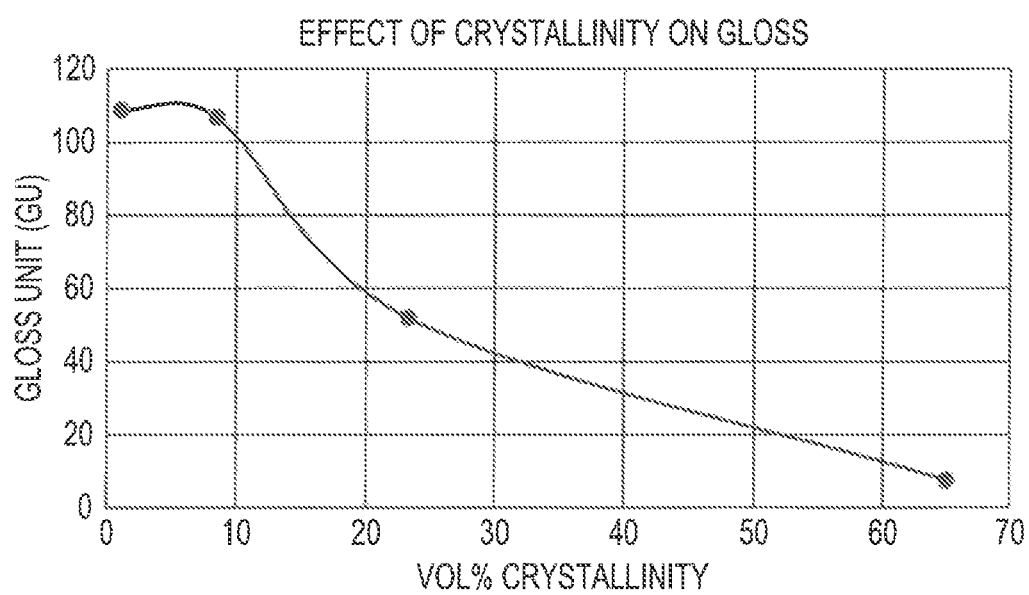
FIG. 15 is a plot showing the measured 60° Gloss Unit values vs. volume percent crystallinity in the Example 2 vitreous enamels.

FIG. 10 shows a photographic side-by-side comparison of the 800° C. heat-treated blade and the 850° C. heat-treated blade. The 850° C. treatment provided a blade with a diffusely reflective and glare-free visible surface having noticeably less surface gloss than the blade subjected to the 800° C. treatment. FIG. 11 through FIG. 14 are photomicrographs of each of the four heat-treated vitreous enamels shown in Table 3, demonstrating the development at increasing heat treatment temperatures of a first crystalline phase (111 in FIG. 11, 121 in FIG. 12, 131 in FIG. 13 and 141 in FIG. 14) with successively larger crystallites at a successively larger volume percent, and the appearance in at least FIG. 14 of a second crystalline phase (143 in FIG. 14). FIG. 15 is a plot showing the measured 60° Gloss Unit values vs. volume percent crystallinity in the vitreous enamel coating.

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

The invention claimed is:

1. An article comprising:
   (a) an electrosurgical cutting blade comprising a metal electrode, and
   (b) a visible vitreous enamel coating on at least a portion of the metal electrode,
   wherein incident light striking the vitreous enamel coating is diffusely reflected or absorbed, and the vitreous enamel coating exhibits a 60° gloss value less than 100 gloss units as measured according to ASTM D523-14, Standard Test Method for Specular Gloss, wherein the vitreous enamel coating contains crystallites in an amount that cause the coating to absorb or scatter incident light.

2. The article of claim 1, wherein the vitreous enamel coating is sufficiently diffusely reflective or absorptive so that the underlying metal electrode is not visible through the coating under typical indoor illumination.

3. The article of claim 1, wherein the vitreous enamel coating is sufficiently diffusely reflective or absorptive so that a specular second surface reflection from the underlying metal electrode is not visible through the coating during plasma operation.

4. The article of claim 1, wherein the vitreous enamel coating diffusely reflects or absorbs light in a visible light wavelength band of interest.

5. The article of claim 1, wherein the vitreous enamel coating diffusely reflects or absorbs light in an infrared light wavelength band of interest.

6. The article of claim 1, wherein the vitreous enamel coating contains a non-infrared-absorptive inorganic pigment.

7. The article of claim 1, wherein the vitreous enamel is an amorphous glass composition.

8. The article of claim 1, wherein the vitreous enamel is a glass-ceramic composition having a crystalline phase.

9. The article of claim 1, wherein the metal electrode is etched or otherwise roughened so that incident light passing into the vitreous enamel coating will not be specularly reflected by the metal electrode.

10. The article of claim 1, wherein a non-specularly reflective coating is applied between the metal electrode and the vitreous enamel coating, so that incident light passing into the vitreous enamel coating will not be specularly reflected by the metal electrode.

11. The article of claim 1, wherein the vitreous enamel coating discourages reflection of visible or other light in colors that might interfere with markers, sensors or other instruments that measure light emitted by or passing through nearby tissue.

12. The article of claim 1, wherein the vitreous enamel coating contains sufficient pigment or colorant, or has sufficient crystallinity, so that the metal electrode is not visible through the coating under typical indoor illumination.

13. The article of claim 1, wherein the vitreous enamel coating contains sufficient pigment or colorant, or has sufficient crystallinity, so that a specular second surface reflection from the metal electrode is not visible through the coating during plasma operation.

14. The article of claim 1, wherein the vitreous enamel comprises an aluminoborosilicate glass.

15. The article of claim 1, wherein the vitreous enamel is formed from a glass frit comprising $SiO_2$, $B_2O_3$, $Al_2O_3$, and optionally one or more of SrO, BaO, CaO, MgO, ZnO, $Na_2O$, $K_2O$ or a combination thereof.

16. The article of claim 1, wherein the metal electrode is titanium, tantalum, molybdenum, tungsten, stainless steel, or an alloy thereof.

17. The article of claim 1, further comprising an insulated handle attached to the electrosurgical cutting blade and housing at least one conductor that can connect the metal electrode to a radiofrequency energy power supply.

18. An article comprising:
   (a) an electrosurgical cutting blade comprising a metal electrode, and
   (b) a visible vitreous enamel coating on at least a portion of the metal electrode,
   wherein incident light striking the vitreous enamel coating is diffusely reflected or absorbed, and the vitreous enamel coating exhibits a 60° gloss value less than 100 gloss units as measured according to ASTM D523-14, Standard Test Method for Specular Gloss, and wherein a visible outer surface of the vitreous enamel coating is etched or otherwise roughened to cause the coating to not specularly reflect incident light.

19. An article comprising:
   (a) an electrosurgical cutting blade comprising a metal electrode, and
   (b) a visible vitreous enamel coating on at least a portion of the metal electrode,
   wherein incident light striking the vitreous enamel coating is diffusely reflected or absorbed, and the vitreous enamel coating exhibits a 60° gloss value less than 100 gloss units as measured according to ASTM D523-14, Standard Test Method for Specular Gloss, and wherein the vitreous enamel coating contains sufficient refractive inorganic pigment to cause the coating to absorb or scatter incident light, wherein the inorganic pigment is more refractive than the vitreous enamel coating.

* * * * *